US011672625B2

(12) United States Patent
Gazonnet et al.

(10) Patent No.: US 11,672,625 B2
(45) Date of Patent: Jun. 13, 2023

(54) DISPOSABLE PACK FOR A STERILIZED MEDICAL DEVICE, IN PARTICULAR A SURGICAL IMPLANT

(71) Applicant: NOVASTEP, Saint-Gregoire (FR)

(72) Inventors: Lilian Gazonnet, Buellas (FR); Chloé Laroche, Rennes (FR); Loïc Girod, Goven (FR); Grégory Gledel, Paris (FR)

(73) Assignee: NOVASTEP, Saint-Gregoire (FR)

( * ) Notice: Subject to any disclaimer, the term of this patent is extended or adjusted under 35 U.S.C. 154(b) by 127 days.

(21) Appl. No.: 17/437,226

(22) PCT Filed: Feb. 26, 2020

(86) PCT No.: PCT/FR2020/050373
§ 371 (c)(1),
(2) Date: Sep. 8, 2021

(87) PCT Pub. No.: WO2020/183087
PCT Pub. Date: Sep. 17, 2020

(65) Prior Publication Data
US 2022/0168061 A1 Jun. 2, 2022

(30) Foreign Application Priority Data
Mar. 8, 2019 (FR) ..................... 19/02358

(51) Int. Cl.
*A61B 50/30* (2016.01)
*A61B 50/00* (2016.01)

(52) U.S. Cl.
CPC ...... *A61B 50/30* (2016.02); *A61B 2050/0064* (2016.02)

(58) Field of Classification Search
CPC .................. A61B 50/30; A61B 2050/0064
USPC ................................... 206/63.5, 438
See application file for complete search history.

(56) References Cited

U.S. PATENT DOCUMENTS

| 7,490,723 | B2 * | 2/2009 | Levisman | A61J 1/065 |
| | | | | 215/47 |
| 8,413,811 | B1 | 4/2013 | Arendt | |
| 2003/0221977 | A1 * | 12/2003 | Kumar | A61C 8/0087 |
| | | | | 206/63.5 |
| 2004/0112781 | A1 * | 6/2004 | Hofverberg | A61C 8/0087 |
| | | | | 206/363 |
| 2007/0181446 | A1 | 8/2007 | Donahoe et al. | |

(Continued)

FOREIGN PATENT DOCUMENTS

EP 3 153 128 A1 4/2017
WO 2018/081339 A1 5/2018

OTHER PUBLICATIONS

Apr. 30, 2020 Search Report issued in International Patent Application No. PCT/FR2020/050373.

*Primary Examiner* — Jacob K Ackun
(74) *Attorney, Agent, or Firm* — Oliff PLC

(57) ABSTRACT

A packaging for a medical device including at least: a support including at least a first end and a second end opposite the first end, wherein the support is deformable between at least: a storage position in which the support is arranged fully inside in the outer casing, a display position, in which the support is arranged outside the outer casing and the first portion and the second portion of the support each extend along a secant axis to the third portion.

13 Claims, 12 Drawing Sheets

(56) References Cited

U.S. PATENT DOCUMENTS

| | | | | |
|---|---|---|---|---|
| 2011/0247947 | A1* | 10/2011 | Nihei | A61C 8/0087 |
| | | | | 206/63.5 |
| 2022/0061948 | A1* | 3/2022 | Richart | A61B 50/22 |

* cited by examiner

[Fig. 1]
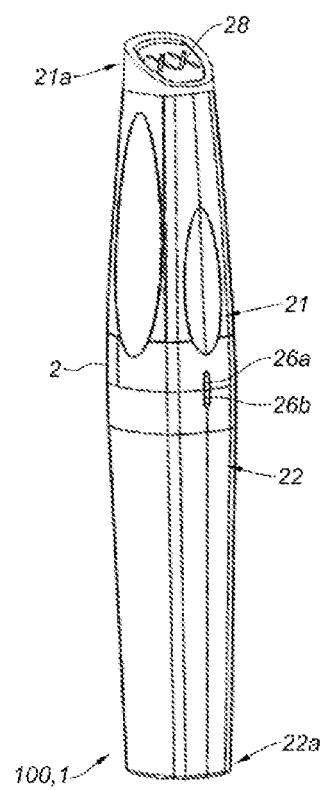

[Fig. 2]
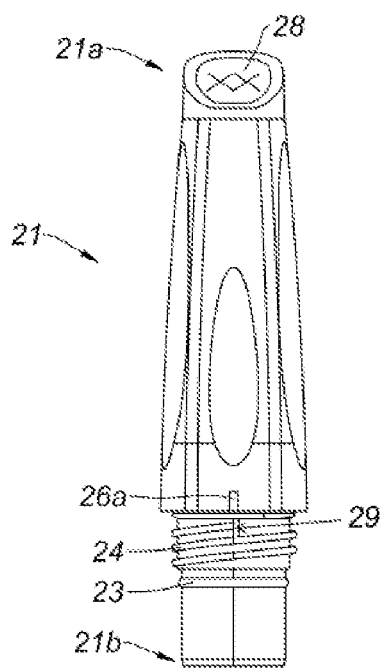
[Fig. 3]
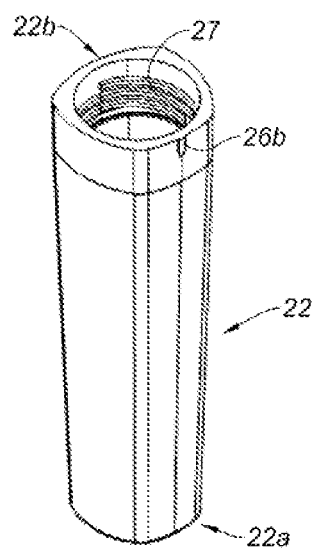

[Fig. 4]
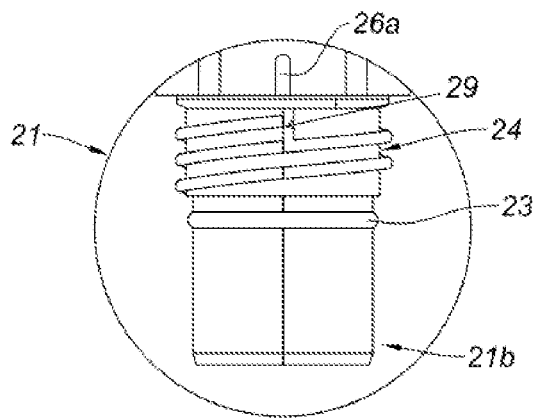
[Fig. 5]
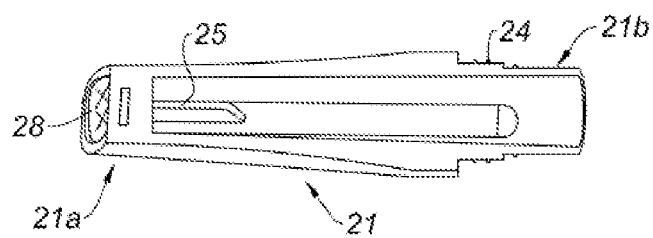
[Fig. 6]
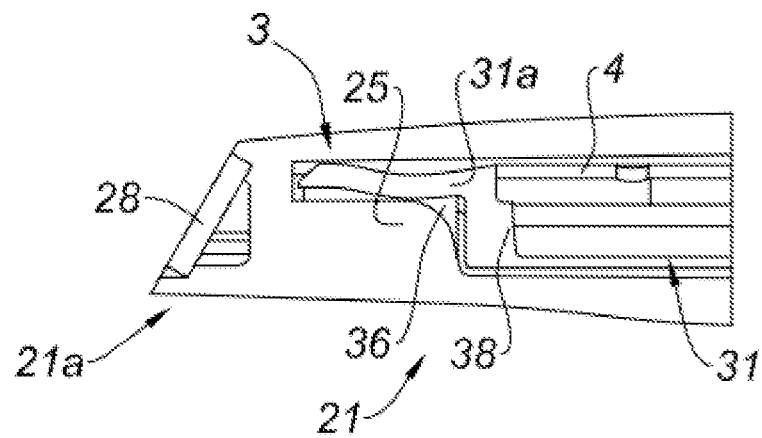

[Fig. 7]
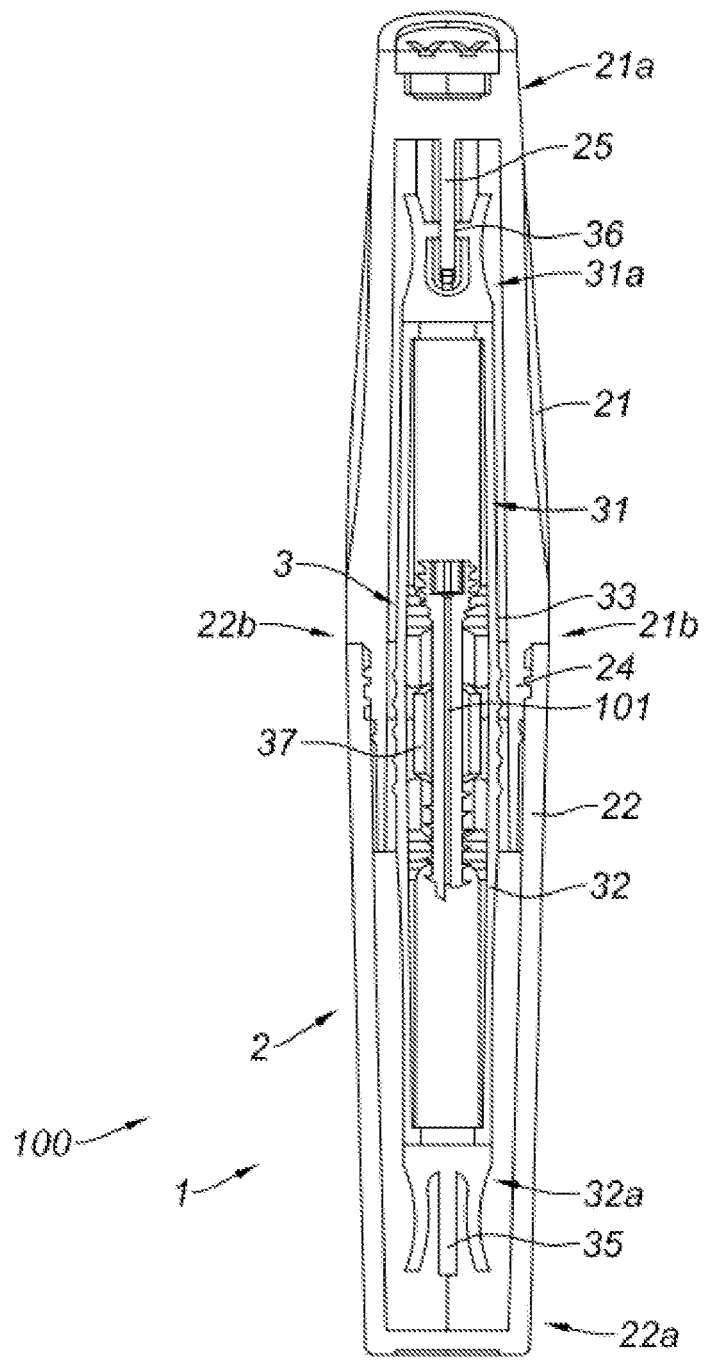

[Fig. 8]
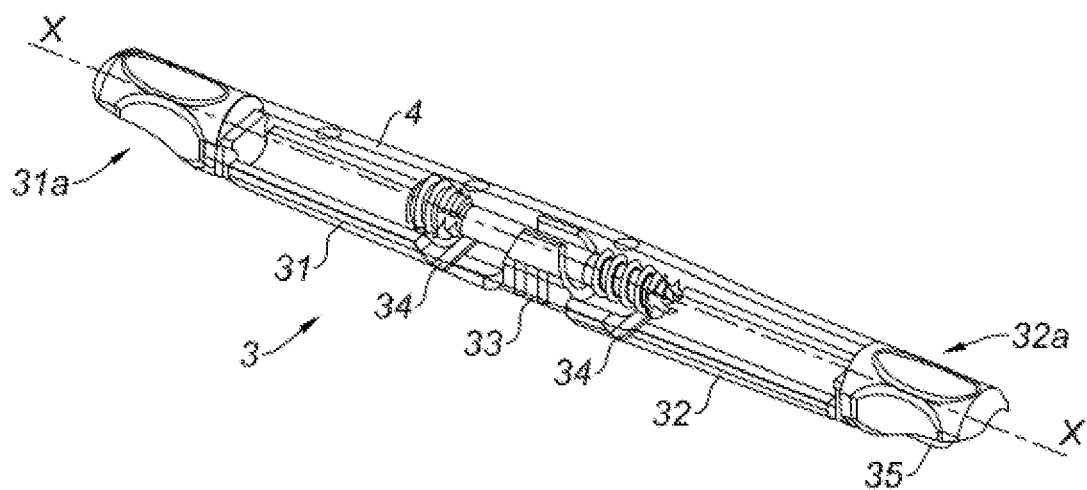
[Fig. 9]
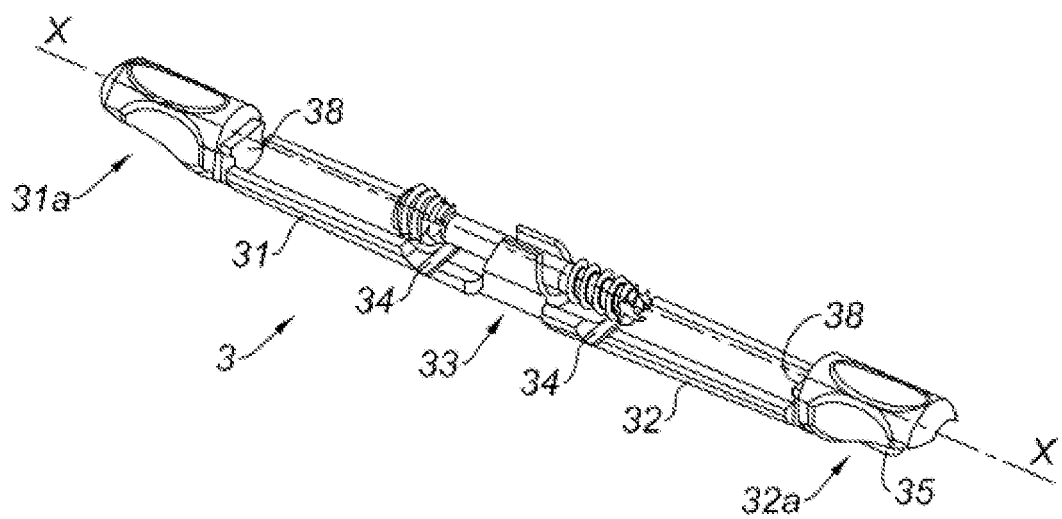

[Fig. 10]
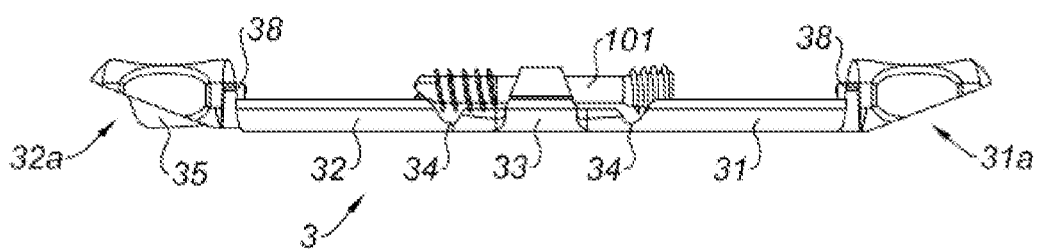
[Fig. 11]
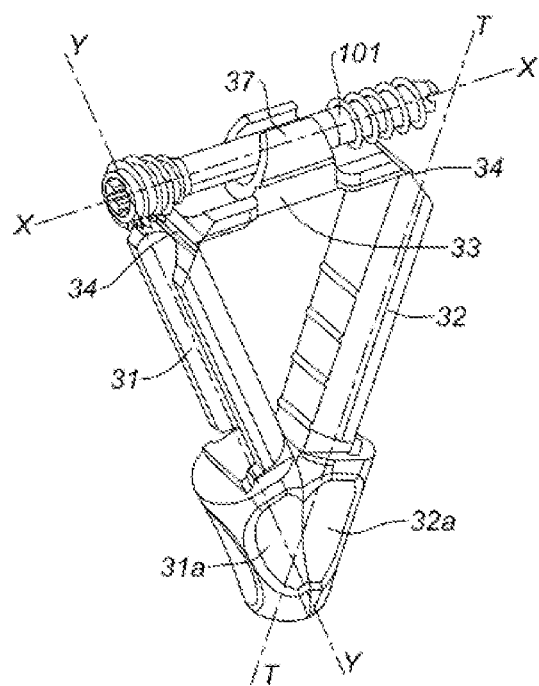

[Fig. 12]
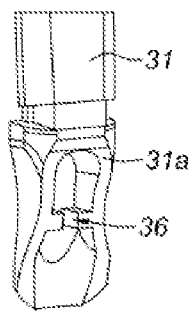
[Fig. 13]
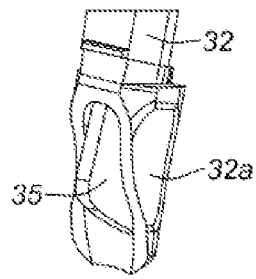
[Fig. 14]
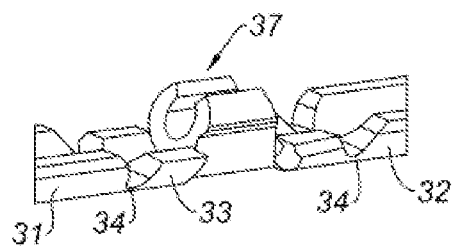

[Fig. 15]
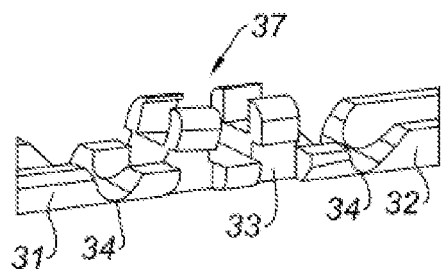
[Fig. 16]
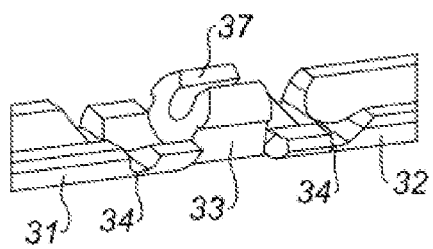
[Fig. 17]
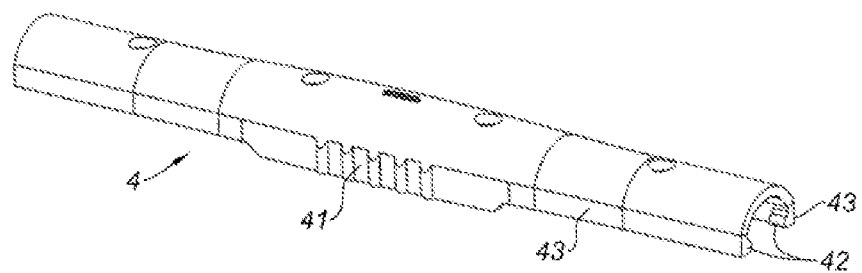

[Fig. 18]
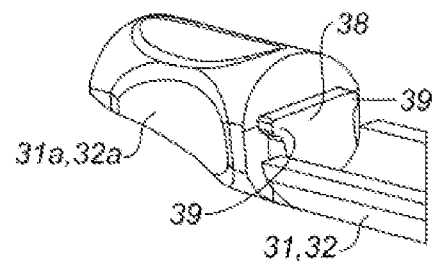
[Fig. 19]
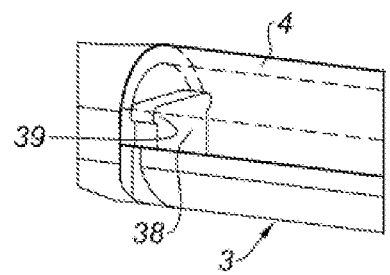
[Fig. 20]
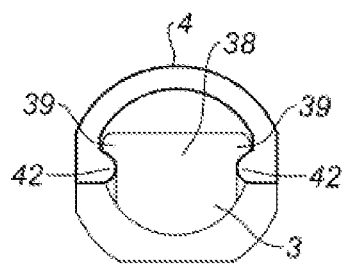

[Fig. 21]
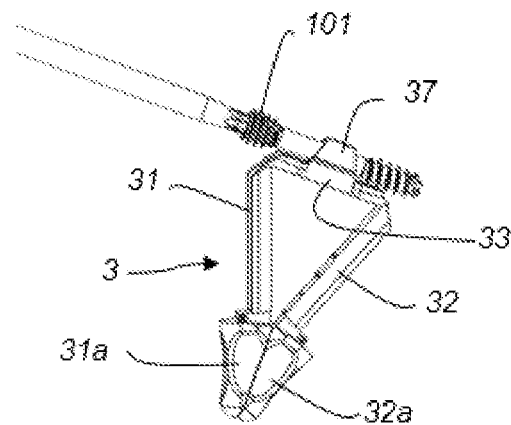
[Fig. 22]
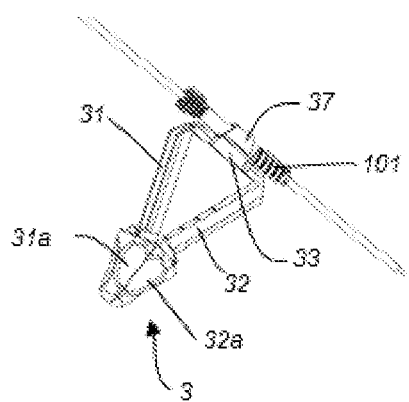

[Fig. 23]
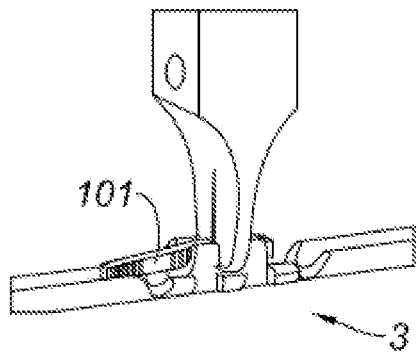
[Fig. 24]
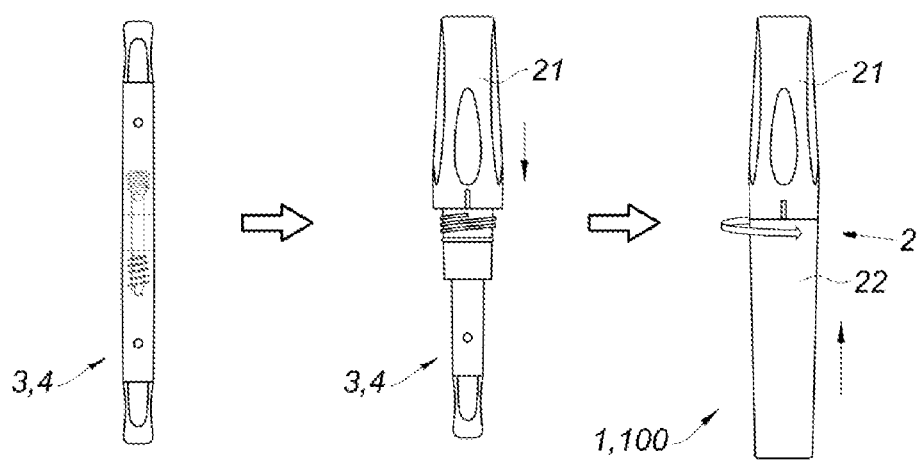
[Fig. 25]
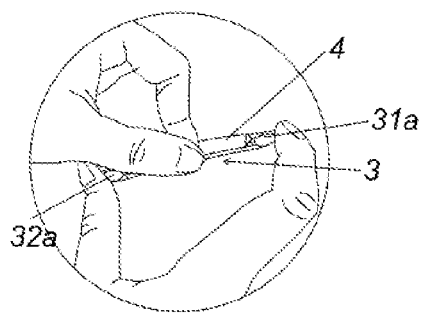

[Fig. 26]
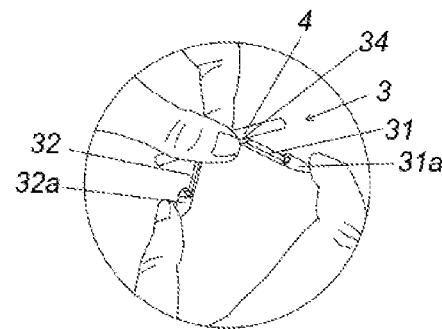
[Fig. 27]
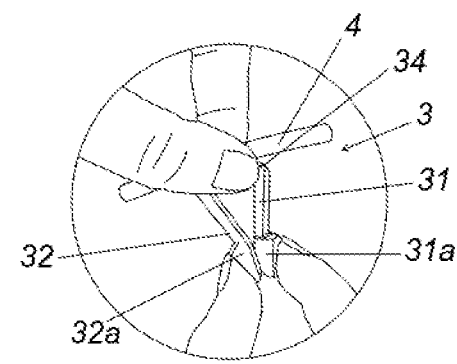
[Fig. 28]
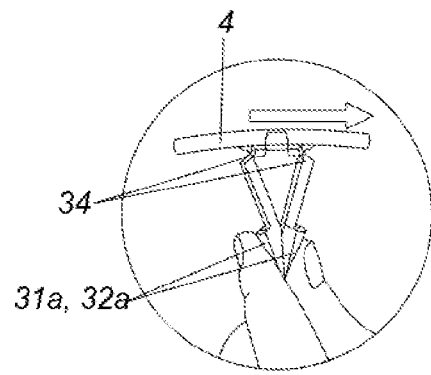

DISPOSABLE PACK FOR A STERILIZED MEDICAL DEVICE, IN PARTICULAR A SURGICAL IMPLANT

TECHNICAL FIELD OF THE INVENTION

The invention concerns the technical field of packs, preferably intended for one single use, for the sterilized packing and transport of medical devices and in particular of surgical implants, in the context of surgeries.

In the present application, by «medical devices», it should be understood any device intended for medical use, including surgical implants and set-up instruments.

STATE OF THE ART

During surgeries, the surgeon could be brought to use sterilized surgical implants and to implant them in the body of the patient using a dedicated and sterilized instrumentation. The medical devices may be supplied unsterilized to the healthcare facility, that is to say housed in a container integrating one or several medical device(s) intended to be sterilized by the healthcare facility in an autoclave prior to the surgery.

Alternatively, the medical devices may be supplied sterilized in an individual and dedicated pack, requiring no sterilization by the healthcare facility. For this type of packs, the way in which the implant and a portion of the pack are sterilized is generally the gamma-ray irradiation. These disposable sterilized individual packs have many advantages. Indeed, the sterility and the traceability of the implant are guaranteed, which allows ensuring safety of the patient; the facility does not have to sterilize the implants beforehand, which improves logistics in the healthcare facility; and the implant is made available immediately and in several number for several distinct services for example traumatology, general surgeries.

In some individual packages of sterilized medical devices, the pack has an inner volume within which the medical is free, that is to say no retaining member is provided to fix the medical device in position within the pack. These packages have the drawback of not being able to guarantee the integrity of the medical device disposed thereinside. Indeed, the latter being free in a closed volume, it could be broken or deteriorated thereinside by hitting the walls of the pack. Furthermore, the user often has to make it fall off the pack to take it out and use it, this manipulation could also damage it and/or alter the sealing of the package thereby compromising its sterilized nature.

In some packages, in the inner volume of the pack, said medical device is retained by a support, fixing the medical device in position within the pack, said support allowing retrieving it by means of adapted instruments. The support of these packs may be in several forms such as hooks, clamps, lugs, etc. The support of these packs may be elastically deformable thereby enabling the release of the implant and the gripping thereof by an adapted instrument.

However, the previously-described current technical solutions have many drawbacks. Indeed, the way in which the medical device is gripped requires either a manual handling of the medical device or the use of a specific instrumentation to retrieve the implant. Furthermore, the handling area of the medical device is on the same longitudinal axis as the handling area of its support which could result in ergonomic problems. Moreover, in some packs, only one end of the medical device is accessible thereby enabling only manual handling or using a screwdriver while preventing a possible direct insertion on a guide wire as usually done in surgery and in particular in orthopaedics.

OBJECT OF THE INVENTION

In particular, the object of the invention concerns disposable packs for implants provided with a support configured to retain the implant in said pack, said support allowing holding the medical device during transport and allowing facilitating gripping and use thereof.

The invention aims to overcome all or part of the aforementioned drawbacks and in particular optimize the support, in order to guarantee the integrity of the medical device within the pack while preserving compactness and ergonomic and easy use and gripping.

To this end, an object of the invention is a pack for a medical device comprising at least:
  a hollow outer case comprising at least one plug and a body, configured to cooperate with one another so as to delimit a closed inner volume in which a medical device is intended to be disposed,
  a support comprising at least one first end and one second end opposite to the first end, a first portion including the first end, a second portion including the second end and a third portion arranged between the first portion and the second portion, said support further comprising at least one retaining member configured to retain the medical device, said retaining member being formed on the third portion of the support, characterized in that the support is deformable between at least:
  a stowing position in which the support is completely arranged within the outer case, the first end of the support is housed in the body of the outer case and the second end is housed in the plug of the outer case, and the first portion and the second portion are aligned with the third portion of the support according to a longitudinal axis of the support,
  a presentation position, in which the support is arranged outside the outer case and each of the first portion and the second portion of the support extends according to an axis secant to the third portion.

The advantage of such a pack lies in that the latter ensures the preservation of the sterility of the medical device during transport thereof till final use thereof, while allowing for an ergonomic, simple and intuitive availability of the medical device, with as little parts and manipulations as possible. Furthermore, with this type of packs according to the invention, it is possible to package a wide range of references of medical devices.

According to a feature of the invention, the first portion is hinged relative to the third portion of the support. Preferably, the first portion is joined to the third portion by a film hinge.

In the present invention, a film hinge is an area with a weakened thickness in comparison with the overall thickness of the support.

According to a feature of the invention, the second portion is hinged relative to the third portion of the support. Preferably, the second portion is joined to the third portion by a film hinge.

According to a feature of the invention, the deformation of the support is achieved by exercising a pressure on the first end and on the second end in a direction substantially perpendicular to or at least secant with respect to the longitudinal axis of the support.

Advantageously, the first end and the second end of the support are configured to cooperate with one another in the presentation position of the support. The cooperation of the first end with the second end allows securing the presentation position and creating a gripping portion such as a handle enabling holding of the support during the removal of the medical device.

According to a feature of the invention, the first end or the second end comprises a projecting lug and respectively, the second end or the first end comprises a groove shaped so as to cooperate with the projecting lug. Advantageously, the projecting lug and the groove are dimensioned to ensure holding in position by wedging.

According to a feature of the invention, the pack comprises a protective part configured to protect the medical device, for example from a contact with the hands of the operator. Advantageously, the protective part is configured to cooperate with the support.

According to a feature of the invention, the protective part is elongate shaped.

According to a feature of the invention, the protective part has two opposite longitudinal edges intended to cooperate with the support.

According to a feature of the invention, the protective part comprises at least one pair of studs shaped so as to cooperate with a coupling lug of the support, each of the studs of the pair being arranged on a longitudinal edge and preferably opposite one another.

Preferably, the protective part comprises a pair of studs at each end.

Alternatively, according to the invention, the studs may be replaced by a longitudinal rib formed at least partially on each longitudinal edge.

According to a feature of the invention, the protective part is at least partially translucent or transparent, which allows seeing the medical device through said protective part.

According to a feature of the invention, the support comprises at least one coupling lug configured to cooperate with the protective part.

According to a feature of the invention, the coupling lug cooperates with the protective part by interlocking and/or by an at least partial shape matching.

According to a feature of the invention, the shape of the retaining member is adapted according to the fastening stress of the medical device and its geometry.

According to a feature of the invention, the third portion of the support is centered with respect to the first and second portions of the support.

According to a feature of the invention, the plug of the outer case is hollow.

According to a feature of the invention, the body of the outer case is hollow.

According to a feature of the invention, the outer case has a generally cylindrical shape, for example in the form of a closed tube.

According to a feature of the invention, the closed inner volume of the outer case is sealed.

According to a feature of the invention, the plug of the outer case comprises a closed end and an opposite open end.

According to a feature of the invention, the body of the outer case comprises a closed end and an opposite open end.

According to a feature of the invention, the open end of the plug is configured to cooperate with the open end of the body of the outer case.

According to a feature of the invention, the open end of the body further comprises a sealing member, for example an O-ring gasket, configured to ensure sealing of the closed inner volume of the outer case.

According to a feature of the invention, the thread is formed on the open end of the body and is shaped so as to cooperate with a complementary thread formed on the plug of the case.

According to a feature of the invention, a complementary thread is formed on the open end of the plug and is shaped so as to cooperate with a thread formed on the body of the case.

According to a feature of the invention, the plug and the body of the outer case cooperate by screwing. Advantageously, upon screwing of the plug on the body of the outer case, the sealing member is deformed and collapses against the plug, so as to ensure sealing between the plug and the body of the outer case.

According to a feature of the invention, the sealing member may be made of a material different from that of the body.

According to a feature of the invention, the sealing member may be made of a material having a lower rigidity than the rigidity of the materials in which the body of the outer case and the plug are made. Alternatively, the sealing member may be made of a material having a lower rigidity than the rigidity of the material in which the plug is made.

According to a feature of the invention, each of the plug and the body of the outer case comprises an index element. Advantageously, the index elements are configured to assist in the positioning of the plug with respect to the body before screwing of the plug on the body and to allow confirming that the plug is properly completely screwed on the body, thereby locking the pack and guaranteeing sealing of the latter.

According to a feature of the invention, each of the plug and the body of the outer case comprises an index element, the index element of the plug being configured to coincide with the index element of the body at the beginning of screwing and on completion of screwing.

According to a feature of the invention, before complete closure of the plug on the body, that is to say before screwing of the plug on the body, the index element of the plug is positioned opposite the index element of the body of the outer case, the index element of the plug and the index element of the body of the outer case being aligned according to a longitudinal axis.

According to a feature of the invention, after complete closure of the plug on the body, that is to say after complete screwing, the index element of the plug and the index element of the body of the outer case are aligned according to a longitudinal axis, in order to confirm the complete screwing of the plug on the body.

According to a feature of the invention, the index element of the plug and/or the index element of the body is a relief or a pattern, such as a groove, a rib, a color code, a figure element, etc. This index allows ensuring a perfect matching between the plug and the body when the outer case is closed.

According to a feature of the invention, the thread formed on the open end of the body has a stop element configured to come into contact with the thread formed on the open end of the plug. This stop element allows ensuring the contact between the plug and the body upon completion of screwing and a perfect matching with the body.

According to a feature of the invention, the closed end of the body has a housing adjusted to the first end of the support.

According to a feature of the invention, the closed end of the plug has a housing adjusted to the second end of the support.

According to a feature of the invention, when the support is in the stowing position, the first end of the support is assembled with the closed end of the body.

According to a feature of the invention, the second end of the support is covered by the closed end of the plug.

Advantageously, sealing, and therefore the preservation of the sterilized barrier, is achieved by completing screwing of the plug on the body.

According to a feature of the invention, the assembly of the first end of the support with the closed end of the body is achieved by wedging of the first end of the support in the closed end of the body.

According to a feature of the invention, the assembly of the closed end of the plug with the second end of the support is achieved by coverage of the second end of the support in the closed end of the plug.

According to a feature of the invention, the closed end of the body comprises an inner rib shaped so as cooperate with a groove formed on the first end of the support. Advantageously, the groove formed on the first end of the support is the same one for cooperating with the inner rib of the end of the body and for cooperating with the projecting lug of the second end.

Alternatively, the closed end of the plug comprises an inner rib shaped so as to cooperate with a groove formed on the second end of the support. Advantageously, the groove formed on the second end of the support is the same one for cooperating with the inner rib of the end of the plug and for cooperating with the projecting lug of the first end.

According to a feature of the invention, the support is detached from the outer case by translation according to the longitudinal axis of the outer case, while a protection of the medical device is maintained According to a feature of the invention, the body of the case has a so-called unsterilized handling area corresponding to the entire body except the threaded open end, which is configured to fit into the open end of the plug.

According to a feature of the invention, the support comprises a so-called unsterilized handling area, which corresponds to the portions of the support that project from the body of the outer case, when the plug is pulled off.

Advantageously, the unsterilized handling area of the body and the sterilized handling area of the support have a length long enough to avoid sterility errors, that is to say contact of the sterilized area by the unsterilized operator or vice versa. For example, this length may range from 30 to 60 cm.

According to a feature of the invention, the outer case and/or the support and/or the protective part may be made of a polymer such as polybutylene terephthalate (PBT), high-density polyethylene (HDPE), polypropylene (PP), etc. for example by an injection-type industrial process.

Another object of the invention is a medical device set comprising at least one medical device arranged in a pack according to the invention.

Advantageously, the support of the invention is in the stowing position, and the medical device generally extends in the axis of the support.

Preferably, the medical device is held by its center, which allows clearing the ends of the medical device and facilitating gripping and removal of the latter by an instrument. In particular, the removal of the medical device may be done without contact with the practitioner's gloves for example by means of a screwdriver, by means of a specific clamp, directly on a pre-inserted wire.

According to a feature of the invention, the medical device is preferably sterilized by gamma-ray irradiation for example.

According to a feature of the invention, the pack further comprises a protective sleeve made in the form of a sheath or a heat-shrinkable film in order to ensure sealing of the pack and guarantee inviolability thereof.

BRIEF DESCRIPTION OF THE FIGURES

The invention will be better understood, thanks to the description hereinafter, which relates to embodiments according to the present invention, provided as non-limiting examples and explained with reference to the appended schematic figures. The appended schematic figures are listed hereinbelow:

FIG. 1 illustrates, according to a perspective view, the pack according to the invention.

FIG. 2 illustrates the body of the outer case of the pack according to the invention.

FIG. 3 illustrates the plug of the outer case of the pack according to the invention.

FIG. 4 illustrates, according to a detail view, the open end of the body represented in FIG. 2.

FIG. 5 illustrates, according to a longitudinal sectional view, the inside of the body of the outer case according to the invention.

FIG. 6 illustrates, according to a detail view, the cooperation between the support and the body of the outer case according to the invention.

FIG. 7 illustrates, according to a longitudinal section, the medical device set according to the invention.

FIG. 8 illustrates, according to a perspective view, the support equipped with the protective part according to the invention.

FIG. 9 illustrates, according to a perspective view, the support without the protective part according to the invention.

FIG. 10 illustrates, according to a side view, the support according to the invention in the stowing position.

FIG. 11 illustrates, according to a side view, the support according to the invention in the presentation position.

FIG. 12 illustrates, according to a perspective view, the detail of one end of the support according to the invention.

FIG. 13 illustrates, according to a perspective view, the detail of the other end of the support according to the invention.

FIG. 14 illustrates an embodiment of the retaining member of the support according to the invention.

FIG. 15 illustrates another embodiment of the retaining member of the support according to the invention.

FIG. 16 illustrates another embodiment of the retaining member of the support according to the invention.

FIG. 17 illustrates, according to a perspective view, the protective part according to the invention.

FIG. 18 illustrates, according to a perspective view, one of the ends of the support equipped with a coupling lug according to the invention.

FIG. 19 illustrates, according to a perspective detail view, the assembly of the support and of the protective part.

FIG. 20 illustrates, according to a cross-sectional view, the assembly represented in FIG. 19.

FIG. 21 illustrates the support in the presentation position with an implant, the implant being removed by one of its ends using an instrument.

FIG. 22 illustrates the support in the presentation position with an implant, the implant being positioned directly on a pre-inserted wire.

FIG. 23 illustrates the support in the presentation position with an implant, the implant being removed by its center using a clamp.

FIG. 24 illustrates the main steps of assembly of the pack according to the invention.

FIG. 25 illustrates a first step of removing the protective part in order to access the medical device.

FIG. 26 illustrates a second step of removing the protective part in order to access the medical device.

FIG. 27 illustrates a third step of removing the protective part in order to access the medical device.

FIG. 28 illustrates a fourth step of removing the protective part in order to access the medical device.

DETAILED DESCRIPTION

As illustrated in FIG. 1, the pack 1 according to the invention is intended for the protection of a medical device 101 during transport thereof till use thereof. The medical device 101 may consist of a surgical implant, a medical part, a surgical instrument, etc. The pack according to the invention is intended for one single use, that is to say it is disposable once the medical device 101 is removed. Furthermore, the pack 1 according to the invention allows preserving the sterility of the medical device 101 therewithin as long as the latter is not used.

In the example illustrated in FIGS. 1 to 3, the pack 1 comprises a hollow outer case 2, formed by at least one hollow body 21 and by a hollow plug 22. Advantageously, and as shown in particular in FIG. 1, the outer case 2 has a generally cylindrical shape, for example in the form of a tube.

The body 21 may have a slender shape for example, yet of course, the shape of the body 21 may be anything else, yet without departing from the scope of the invention. As shown, the body 21 comprises a closed end 21a and an opposite open end 21b. Optionally, an element 28 for identifying the type of the medical device contained in said pack 1 may be arranged on the closed end of the body 21 of the outer case 2, that being represented in particular in FIGS. 1 and 2. Advantageously, the open end 21b of the body 21 further comprises a sealing member 23, in this instance represented in FIG. 2, it consists of an O-ring gasket, configured to ensure sealing of the closed inner volume of the outer case 2. As shown in FIG. 2, a thread 24 is formed on the open end 21b of the body 21 and is shaped so as to cooperate with a complementary thread 27 formed on the plug 22 of the outer case 2.

The body 21 of the case 2 has a so-called unsterilized handling area corresponding to the entire body 21 except the threaded open end 21b, which is configured to fit into the open end 22b of the plug 22.

The plug 22 of the outer case 2 is illustrated in FIG. 3. It comprises a close end 22a and an opposite open end 22b. The open end 22b of the plug 22 is configured to cooperate with the open end 21b of the body 21 of the outer case 2.

The body 21 and the plug 22 are configured to cooperate with the one another so as to delimit a sealed closed inner volume within which a medical device 101 is disposed. More particularly, the body 21 and the plug 22 of the outer case 2 cooperate by screwing. Advantageously, upon screwing of the plug 22 on the body 21 of the outer case 2, the sealing member 23 is deformed and collapses against the plug 22, so as to ensure sealing between the plug 22 and the body 21 of the outer case 21.

As illustrated in FIG. 1, each of the body 21 and the plug 22 of the outer case 2 comprises an index element 26a, 26b, the index element 26b of the plug 22 being configured to coincide with the index element 26a of the body 21 at the beginning of screwing and on completion of screwing. In the example illustrated in FIGS. 1, 2 and 3, the index element 26b of the plug 22 and the index element 26a of the body 21 is a relief, for example a groove. As illustrated in FIGS. 2 and 4, the thread 24 formed on the open end 21b of the body 21 has a stop element 29 configured to come into contact with the thread 27 formed on the open end 22b of the plug 22.

The pack 1 further comprises a support 3 represented in particular in FIGS. 7 to 11. The support 3 comprises a first end 31a and a second end 32a opposite to the first end, a first portion 31 including the first end 31a, a second portion 32 including the second end 32a and a third portion 33 arranged between the first portion 31 and the second portion 32, preferably in a centered manner, as shown in particular in FIGS. 9 and 10. Advantageously, the support 3 comprises a handling area, which corresponds to the portions 32, 33 of the support 3 that project from the body of the outer case 2, when the plug 22 is pulled off.

Advantageously, the first portion 31 is hinged relative to the third portion 33 of the support 3 and is preferably jointed to the third portion by a hinge film 34 as illustrated in FIG. 10. Similarly, the second portion 32 is hinged relative to the third portion 33 of the support 3 and is preferably jointed to the third portion 33 by hinge film 34. Of course, the hinge may be in any form and the hinge film example is not restrictive.

The hinge of the first portion 31 and second portion 32 relative to the third portion enables the deformation of the support 3 between at least two positions, a stowing position and a presentation position. Of course, the deformation of the support 3 may be due to the material used to make the support, complementarily with the hinge or alternatively to the hinge, the switch from one position to another then being based on the flexibility of said material.

In the stowing position, as illustrated in FIGS. 7, 8, 9 and 10, the support 3 is completely arranged within the outer case 2, as shown in FIG. 7. The first end 31a of the support 3 is housed in the body 21 of the outer case 2 and the second end 32a is housed in the plug 22 of the outer case 2. In the stowing position, the support extends according to a longitudinal axis X-X and all of its portions 31, 32, 33 are aligned on this axis X-X.

In the presentation position, as illustrated in FIG. 11, the support is taken out the outer case 2, and the first portion 31 and each of the second portion 32 of the support 3 extends according to an axis Y-Y; T-T secant to the longitudinal axis X-X in which only the third portion 33 extends.

Thus, the deformation of the support 3 is advantageously achieved by exercising a pressure on the first end 31a and on the second end 32a in a direction substantially perpendicular to or at least secant with respect to the longitudinal axis X-X of the support 3, causing a rotation of the first 31 and second 32 portions of the support 3 relative to the third portion 33.

In the presentation position and as shown in FIG. 11, the first end 31a and the second end 32a of the support 3 are configured to cooperate with one another. More particularly, in the illustrated example, the first end 31a comprises a groove 36 and the second end 32a comprises a projecting lug 35 which cooperates with the groove 36, as shown in FIGS. 12 and 13.

Quite possibly, this configuration may be reversed, that is to say the first end 31a comprises a projecting lug 35 and the second end 32a comprises a groove 36.

Moreover, the support 3 further comprises a retaining member 37 configured to retain the medical device 101, said retaining member 37 being formed on the third portion 33 of the support 3, as illustrated in particular in FIGS. 9, 10, 11, 14, 15 and 16. Advantageously, the shape of the retaining member 37 is adapted according to the fastening stress of the medical device 101 and the geometry of said medical device 101. In FIGS. 14 to 16, different embodiments of the retaining member are shown: in FIG. 14, the retaining member is a tubular hook; in FIG. 15, the retaining member is formed by two hooks spaced apart with a square-shaped cross-section; and in FIG. 16, the retaining member is formed by a tubular hook whose orifice has a diameter smaller than that of FIG. 14.

In accordance with the invention and in order to add a safety barrier guaranteeing the sterility of the medical device 101, the pack 1 comprises a protective part 4 configured to protect the medical device 101 from contact with the hands of the operator. This protective part 4 is illustrated assembled with the support 3 in FIG. 8 and isolated in FIG. 17. As shown in FIG. 17, the protective part 4 is elongate shaped. The protective part 4 comprises gripping areas 41 with or without a grip enabling sliding or removal of the protective part 4 of the support 3.

Furthermore, the protective part 4 has two opposite longitudinal edges 43 intended to cooperate with the support 3. The protective part 4 comprises at least one pair of studs 42 shaped so as to cooperate with a coupling lug 38 of the support 3, each of the studs 42 of the pair being arranged on one longitudinal edge and preferably opposite to one another. In a non-represented variant, the studs may be replaced by a longitudinal rib formed at least partially on each longitudinal edge. Preferably, the protective part 4 comprises a pair of studs 42 at each end.

As shown in some figures such as FIGS. 9, 10, 18 and 20, the support 3 comprises a coupling lug 38 configured to cooperate with the protective part 4, and arranged at the level of each end 31a, 32a. As shown in FIG. 20, each coupling lug 38 cooperates with the protective part 4 and more particularly with a pair of studs 42 by interlocking and/or by an at least partial shape matching. The coupling lug 38 comprises two symmetrical catches configured to block the protective part 5.

In order to improve the preservation of sterility within the closed inner volume of the outer case 2, the closed end 21a of the body 21 has a housing adjusted to the first end 31a if the support 3. Similarly, the closed end 22a of the plug 22 has a housing intended to accommodate the end 32a of the support 3. Thus, when the support 3 is in the stowing position, the assembly of the first end 31a of the support 3 with the closed end 21a of the support 21 and the coverage of the second end 32a of the support 3 by the closed end 22a of the plug 22, guarantee the sterility of the packaged medical device 101. The assembly of the first end 31a of the support 3 with the closed end 21a of the body 21 is achieved by wedging and the closed end 22a of the plug 22 covers the second end 32a of the support 3. Advantageously, and as illustrated in FIG. 5, the closed end 21a of the body 21 comprises an inner rib 25 shaped so as to cooperate with a groove 36 formed on the first end of the support for example. Advantageously, the groove 36 formed on the first end 31a of the support 3 is the same one for cooperating with the inner rib 25 of the end of the body and for cooperating with the projecting lug 35 of the second end 32a.

The medical device 101 wrapped in its pack 1 according to the invention form a medical device set 100. In this medical device set, the support 3 of the invention is in the stowing position, and the medical device 101 generally extends in the axis X-X of the support 3. As shown in particular in FIG. 7, the medical axis 101 is held by its center, which allows clearing the ends of the medical device and facilitating gripping and removal of the latter by an instrument for example as illustrated in FIGS. 21, 22 and 23. In particular, the removal of the medical device may be done without contact with the practitioner's gloves for example by means of a screwdriver (FIG. 21), by means of a specific clamp (FIG. 23), directly on a pre-inserted wire (FIG. 22).

As illustrated in FIG. 24, the packing procedure would be as follows: the sterilized medical device is placed in the retaining member 37 of the support 3, the support 3 is covered by a protective part 4, the support 3 of the body 21 of the outer case 2 is covered, the plug 22 is disposed opposite the body 21 by aligning the index elements and the plug 22 is screwed until the thread of the plug 22 and the stop element 29 of the body 21 come into contact and the index elements 26a, 26b are aligned.

In FIGS. 25 to 28, are illustrated the steps of removing the protective part 4 in order to access the medical device 101.

In FIG. 25, the ends of the support are grasped with one hand and the protective part 4 is grasped with the other hand. Then, as illustrated in FIG. 26, a pressure is exerted on the first end 31a and on the second end 32a in a direction substantially perpendicular to the support 3 to make them converge beneath the support 3, the first portion 31 and the second portion 32 of the support 3 rotatably pivot at the level of the hinges in the form of film hinges 34, the third portion 33 remaining on its place. Then, the first end 31a and the second end 32a are joined together by making them cooperate so that they form a solid a stable support, as illustrated in FIG. 27. Finally, in FIG. 28, the protective part 4 may be removed by a simple translation/sliding.

The description of the technical features of the invention shall not be limited to the disclosed figures and could integrate design variations such as the possibility of packaging medical devices with larger dimensions (for example by a homothety of the diameter/length of the case and of the support), or any other technical modification allowing improving the ergonomics, the simple use and the bulk management while complying with the features and the advantages set forth hereinbefore.

Of course, the invention is not limited to the embodiments described and represented in the appended figures. Modifications are still possible, in particular with regards to the construction of the various elements or by substitution with technical equivalents, yet without departing from the scope of the invention.

The invention claimed is:

1. A pack for a medical device comprising at least:
   a hollow outer case comprising at least one plug and a body, configured to cooperate with one another so as to delimit a closed inner volume in which a medical device is intended to be disposed,
   a support comprising at least one first end and one second end opposite to the first end, a first portion including the first end, a second portion including the second end and a third portion arranged between the first portion and the second portion, the support further comprising at least one retaining member configured to retain the medical device, the retaining member being formed on the third portion of the support, wherein the support is deformable between at least:

a stowing position in which the support is completely arranged within the outer case, the first end of the support is housed in the body of the outer case and the second end is housed in the plug of the outer case, and the first portion and the second portion are aligned with the third portion of the support according to a longitudinal axis of the support, a presentation position, in which the support is arranged outside the outer case and each of the first portion and the second portion of the support extends according to an axis secant to the third portion.

2. The pack according to claim 1, wherein the first portion is hinged relative to the third portion of the support and/or the second portion is hinged relative to the third portion of the support.

3. The pack according to claim 1, wherein the first end and the second end of the support are configured to cooperate with one another in the presentation position of the support.

4. The pack according to claim 3, wherein the first end or the second end comprises a projecting lug and respectively, the second end or the first end comprises a groove shaped so as to cooperate with the projecting lug.

5. The pack according to claim 1, comprising a protective part configured to protect the medical device, the protective part being configured to cooperate with the support.

6. The pack according to claim 1, wherein the body of the outer case comprises a closed end and an opposite open end.

7. The pack according to claim 6, wherein the open end of the body further comprises a sealing member, configured to ensure sealing of the closed inner volume of the outer case.

8. The pack according to claim 6, wherein the closed end of the body has a housing adjusted to the first end of the support.

9. The pack according to claim 8, wherein the assembly of the first end of the support with the closed end of the body is achieved by wedging of the first end of the support in the closed end of the body.

10. The pack according to claim 1, wherein the plug and the body of the outer case cooperate by screwing.

11. The pack according to claim 10, wherein each of the plug and the body of the outer case comprises an index element, the index element of the plug being configured to coincide with the index element of the body at the beginning of screwing and on completion of screwing.

12. The pack according to claim 1, wherein the support is detached from the outer case by translation according to the longitudinal axis of the outer case.

13. A medical device set comprising at least one medical device arranged in a pack according to claim 1, the support of the pack being in the stowing position, and the medical device extending generally in the axis of the support.

* * * * *